(12) United States Patent
Blaesius et al.

(10) Patent No.: US 11,129,639 B2
(45) Date of Patent: Sep. 28, 2021

(54) METHOD FOR INTEGRATING AN ELECTRICAL CIRCUIT IN A DEVICE AND DEVICE

(71) Applicant: Robert Bosch GmbH, Stuttgart (DE)

(72) Inventors: Jana Blaesius, Ludwigsburg (DE); Aitor Echaniz, Stuttgart (DE); Martin Schoepf, Stuttgart (DE); Michael Walther, Renningen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/633,816

(22) PCT Filed: Jul. 25, 2018

(86) PCT No.: PCT/EP2018/070176
§ 371 (c)(1),
(2) Date: Jan. 24, 2020

(87) PCT Pub. No.: WO2019/020693
PCT Pub. Date: Jan. 31, 2019

(65) Prior Publication Data
US 2020/0170657 A1    Jun. 4, 2020

(30) Foreign Application Priority Data
Jul. 28, 2017   (DE) ................... 10 2017 213 080.6

(51) Int. Cl.
*G06K 19/07* (2006.01)
*A61B 17/32* (2006.01)
(Continued)

(52) U.S. Cl.
CPC .......... *A61B 17/32* (2013.01); *G06K 19/0723* (2013.01); *A61B 17/3201* (2013.01); *A61B 17/3211* (2013.01)

(58) Field of Classification Search
CPC ........ G06K 19/00; G06K 19/04; G06K 19/06; G06K 19/067; G06K 19/07
(Continued)

(56) References Cited

U.S. PATENT DOCUMENTS 6,972,199 B2   12/2005   Lebouitz et al.
8,158,032 B2    4/2012   Liu et al.
(Continued)

FOREIGN PATENT DOCUMENTS

WO   2011/054355 A2   5/2011
WO   2014/017530 A1   1/2014

OTHER PUBLICATIONS

International Search Report corresponding to PCT Application No. PCT/EP2018/070176, dated Oct. 5, 2018 (German and English language document) (5 pages).

*Primary Examiner* — Edwyn Labaze
(74) *Attorney, Agent, or Firm* — Maginot, Moore & Beck, LLP

(57) ABSTRACT

A method integrates an electrical circuit into a device. The device has an integration surface consisting of a first material. The method includes processing the integration surface in order to form connection elements in order to increase an adhesion of a second material to the integration surface. The second material differs from the first material. The method also includes arranging the electrical circuit adjacent to the processed integration surface. The method furthermore includes applying a volume of the second material at least over the integration surface in order to enclose the electrical circuit in a fluid-tight manner.

10 Claims, 9 Drawing Sheets

(51) Int. Cl.
*A61B 17/3201* (2006.01)
*A61B 17/3211* (2006.01)

(58) Field of Classification Search
USPC .............................. 235/492, 487, 380, 375
See application file for complete search history.

(56) References Cited

U.S. PATENT DOCUMENTS

| | | | |
|---|---|---|---|
| 2005/0049564 A1* | 3/2005 | Fabian | A61F 13/36 |
| | | | 604/362 |
| 2005/0223550 A1 | 10/2005 | Launay et al. | |
| 2006/0186210 A1* | 8/2006 | Tethrake | A61B 90/98 |
| | | | 235/492 |
| 2006/0244593 A1* | 11/2006 | Nycz | A61B 90/98 |
| | | | 340/572.1 |
| 2007/0159337 A1* | 7/2007 | Tethrake | G06K 19/041 |
| | | | 340/572.8 |
| 2010/0176925 A1 | 7/2010 | Tethrake et al. | |
| 2011/0079651 A1 | 4/2011 | Tsai et al. | |
| 2012/0245568 A1* | 9/2012 | Yu | A61B 17/32 |
| | | | 606/1 |
| 2013/0069749 A1 | 3/2013 | Singh et al. | |
| 2015/0320506 A1* | 11/2015 | Sayles | A61B 90/98 |
| | | | 235/385 |
| 2017/0258551 A1* | 9/2017 | Smith | G06F 19/00 |

* cited by examiner

METHOD FOR INTEGRATING AN ELECTRICAL CIRCUIT IN A DEVICE AND DEVICE

This application is a 35 U.S.C. § 371 National Stage Application of PCT/EP2018/070176, filed on Jul. 25, 2018, which claims the benefit of priority to Serial No. DE 10 2017 213 080.6, filed on Jul. 28, 2017 in Germany, the disclosures of which are incorporated herein by reference in their entirety.

BACKGROUND

The invention is based on a device or a method of the generic type in the independent claims.

Integration of a sensor system, such as e.g. RFID chips (RFID=Radio-Frequency Identification; identification with the aid of electromagnetic waves), can be applied, inter alia, for example in the field of servicing and maintenance and in the field of logistics often can. Often in this context an RFID transponder can be temporarily secured, e.g. adhesively bonded, to specific locations and tools.

U.S. Pat. No. 6,972,199 B2 relates to a cutting instrument having a multiplicity of sensors integrated therein, and to a sensor system embedded in semiconductor material.

SUMMARY

Against this background, a method and a device as claimed in the main claims are presented with the approach presented here. Advantageous developments and improvements of the device specified in the independent claim are possible by virtue of the measures presented in the dependent claims.

In accordance with embodiments, in particular, a tool or some other device can be realized as a composite part composed of two materials with an integrated electrical circuit, wherein, in the interface region between the two materials, a plurality of connection elements for increasing an adhesion between the materials are shaped from a first one of the materials. An integration of electrical circuits in particular a sensor system, can advantageously be realized by means of a novel design of tools, surgical instruments or other devices as composite parts, for example as metal-plastic composite parts.

It is thus possible to achieve a fixed and tight connection between the materials, for example a metal tool and an applied plastic volume, in which the electrical circuit can be embedded. In order to realize a reliable connection location between the materials, it is possible to provide connection elements, for example in the form of cutouts, in a section of the device which comprises the first material, around which connection elements the second material can flow for example during the process of applying the second material, for example injection molding of plastic, and they thus enable a robust envelopment or anchoring of the second material on the connection elements. It is thus possible to realize a tool or some other device as a composite part, in particular a plastic-metal composite part, in order to enable a durable, permanent and sterilization-stable possibility for integrating electrical circuits in metallic tools, for example.

A method for integrating an electrical circuit in a device is presented, wherein the device has an integration surface composed of a first material, and wherein the method comprises at least the following steps:

processing the integration surface in order to shape connection elements for increasing an adhesion of a second material to the integration surface, wherein the second material differs from the first material;

arranging the electrical circuit adjacent to the processed integration surface; and applying a volume of the second material at least over the integration surface in order to enclose the electrical circuit in a fluid-tight manner.

The device can be a tool, a tool appertaining to medical technology, surgical instruments or the like. The electrical circuit can be realized on a printed circuit board or the like. The electrical circuit can additionally or alternatively have electronic component parts or components. The first material can be a metallic material. The second material can be a plastic. In the step of processing, a surface material of the integration surface can be deformed in order to shape the connection elements. The integration surface can comprise a partial section of a surface of the device that is provided for integrating the electrical circuit. In this case, the integration surface can be arranged in a section or partial section of the device that comprises the first material. The integration surface can constitute a layer, for example a boundary layer, of the first material. In the step of arranging, the electrical circuit can be applied directly to the integration surface and be in direct contact with the integration surface. Adjacent can represent adjoining directly or adjoining indirectly with an air gap or production-dictated interspace. In the step of arranging, the electrical circuit can be applied on or above a region of the integration surface. In the step of applying, the second material can be applied to the electrical circuit. Advantageously, the connection elements can have a positive effect with regard to electromagnetic shielding of the electrical circuit. Moreover, the connection elements can have a positive effect on the stability of the connection between the first and second materials. Optionally, at least one partial section of the part of the device that comprises the first material can have been or be shaped by means of an additive manufacturing process.

In accordance with one embodiment, in step of processing, grid elements, recesses, loops, projection sections, angular elements, cavities having undercuts and additionally or alternatively cavities for increasing a roughness value can be shaped as connection elements. Such an embodiment affords the advantage that a reliable and robust connection between the different materials can be achieved using means that are inexpensive and structurally simple to realize. Suitable connection elements can be selected flexibly here depending on the application and in a material-dependent manner.

Moreover, in step of processing, the connection elements can be shaped by means of laser structuring, spark erosion, forming and additionally or alternatively machining. Such an embodiment affords the advantage that well known and available processing techniques can be used for accurately shaping the connection elements.

Additionally or alternatively, in step of processing, at least the connection elements can be shaped by means of an additive manufacturing process. The additive manufacturing process can be 3D printing or three-dimensional printing, for example. Such an embodiment affords the advantage that even complex structures can be produced accurately, simply and reliably.

Furthermore, in step of processing, at least one portion of the connection elements can be shaped as at least one antenna for signals to and additionally or alternatively from the electrical circuit. The device can thus have at least one antenna which is formed or shaped by the connection elements. In this case, the electrical circuit can be connectable or connected to the connection elements in a manner enabling signal transmission. Such an embodiment affords the advantage that signals can be transmitted and received in an amplified and optionally directional manner to and/or from the electrical circuit.

In this case, the at least one antenna can be shaped as a helical antenna, as a helical antenna having radial microcavities, as a rectangular antenna and additionally or alternatively as a butterfly antenna. Such an embodiment affords the advantage that a type of antenna that is tuned and thus suited to the specific application and a frequency of the electrical circuit can be selected.

In this case, a plurality of antennas aligned in different dimensions can also be shaped. The plurality of antennas can be formed or shaped by three-dimensionally aligned or three-dimensional connection elements. Such an embodiment affords the advantage that it is possible to realize reliable signal transmission in different spatial directions and/or from different spatial directions in a space-saving and inexpensive manner.

Moreover, in this case, in step of processing, at least one depression section can be shaped in the integration surface, wherein the at least one depression section has a parabolic depression profile. Such an embodiment affords the advantage that a parabolic mirror for improving a behavior of the at least one antenna can be provided in a simple manner. Directional emission of signals can thus be reliably achieved.

Furthermore, in step of arranging, an electrical circuit can be arranged which can have at least one detection unit for detecting a physical variable and additionally or alternatively a signal transmission unit for transmitting signals to and additionally or alternatively from the electrical circuit. The physical variable can represent a temperature, an acceleration or the like. Such an embodiment affords the advantage that position determination or finding of the device and additionally or alternatively detection of a specific treatment of the device, for example as a result of the influence of a temperature, can be made possible or facilitated.

In accordance with one embodiment, in step of arranging, the electrical circuit can be encapsulated with an encapsulation material and/or can be provided with a thermal protection layer. Such an embodiment affords the advantage that, with regard to the step of applying, the electrical circuit can thus be protected against an influence of the second material and additionally or alternatively a temperature. Furthermore, a lifetime can be lengthened and a thermal use range of the electrical circuit can be increased.

Also presented is a device having at least the following features:

an integration surface composed of a first material, wherein connection elements for increasing an adhesion of a second material to the integration surface are shaped on the integration surface, wherein the second material differs from the first material;

an electrical circuit arranged adjacent to the processed integration surface; and a volume of the second material applied at least over the integration surface for enclosing the electrical circuit in a fluid-tight manner.

The electrical circuit can be integrated in the device by carrying out steps of an embodiment of the method mentioned above.

By way of example, the device can be shaped as a medical device, and the integration surface can be shaped on a handle of the medical device.

BRIEF DESCRIPTION OF THE DRAWINGS

Exemplary embodiments of the approach presented here are illustrated in the drawings and are explained in greater detail in the following description.

In the figures.

DETAILED DESCRIPTION

In the following description of expedient exemplary embodiments of the disclosure, identical or similar reference signs are used for the elements having a similar effect that are illustrated in the various figures, a repeated description of these elements being dispensed with.

Figure 1:
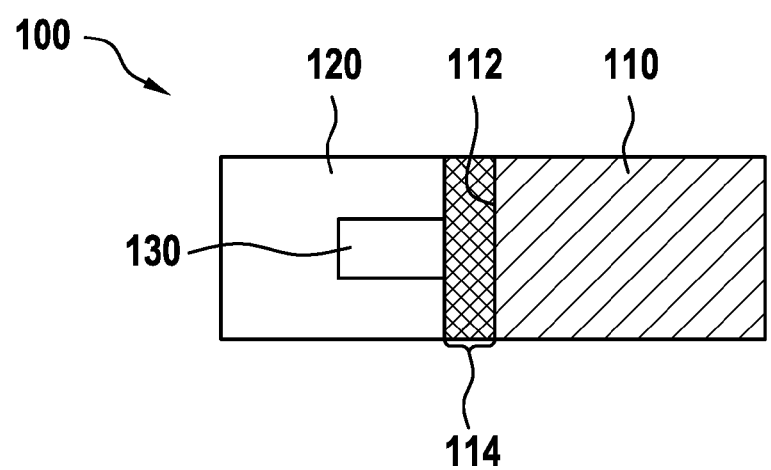
FIG. 1 shows a schematic illustration of a device in accordance with one exemplary embodiment.

FIG. 1 shows a schematic illustration of a device 100 in accordance with one exemplary embodiment. The device 100 is a tool, for example a medical device, such as, for example surgical instruments or the like, or some other type of device.

The device 100 has a volume of a first material 110. The first material 110 is a metal material, for example. The volume of the first material 110 has an integration surface 112. The integration surface 112 is thus shaped from the first material 110. Furthermore, a plurality of connection elements 114 are shaped on the integration surface 112 by means of the processing of the integration surface 112 or the first material 110.

Moreover, the device 100 has a volume of a second material 120. The second material 120 differs from the first material 110. The second material 120 is a plastic material, for example. The volume of the second material 120 adjoins the volume of the first material 110 at the integration surface 112 and the connection elements 114. The connection elements 114 are shaped in order to increase an adhesion of a second material 120 to the integration surface 112 or to the first material 110.

The device 100 furthermore has an electrical circuit 130. The electrical circuit 130 is arranged adjacent to the integration surface 112. The volume of the second material 120 is applied at least over the electrical circuit 130 and the integration surface 112. The electrical circuit 130 is enclosed in a fluid-tight manner by means of the volume of the second material 120.

In accordance with one exemplary embodiment, the electrical circuit 130 is embodied in the form of a radio chip or the like. The electrical circuit 130 can have for example a detection unit for detecting a physical variable and/or a signal transmission unit for transmitting signals.

In accordance with the exemplary embodiment illustrated in FIG. 1, the connection elements 114 are shaped as grid elements. Additionally or alternatively, connection elements 114 in accordance with one exemplary embodiment are shaped as at least one antenna for signals to and/or from the electrical circuit. In accordance with other exemplary embodiments, the connection elements 114 can additionally or alternatively be shaped as recesses, loops, projection sections, angular elements, cavities having undercuts and/or cavities for increasing a roughness value.

In accordance with various exemplary embodiments, a height of the connection elements 114 can be in the nanometers, micrometers or millimeters range.

Figure 2:
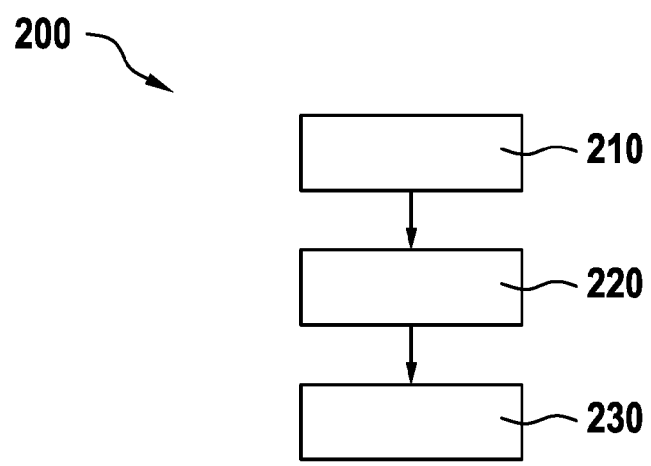
FIG. 2 shows a flow diagram of an integrating method in accordance with one exemplary embodiment.

FIG. 2 shows a flow diagram of an integrating method 200 in accordance with one exemplary embodiment. The integrating method 200 is implementable in order to integrate an electrical circuit in a device. In this case, the integrating method 200 is implementable in order to produce or manufacture the device from FIG. 1 by means of the electrical circuit being integrated in the device 100. To put it another way, the integrating method 200 is implementable in conjunction with a device having an integration surface composed of a first material.

In a step 210 of processing, in the integrating method 200, the integration surface is processed in order to shape connection elements for increasing an adhesion of a second material to the integration surface. The second material differs from the first material.

Afterward, in a step 220 of arranging, the electrical circuit is arranged adjacent to the integration surface that has been processed in step 210 of processing. In a step 230 of applying, a volume of the second material is applied at least over the integration surface in order to enclose the electrical circuit in a fluid-tight manner.

By way of example, in step 210 of processing, grid elements, recesses, loops, projection sections, angular elements, cavities having undercuts and/or cavities for increasing a roughness value are shaped as the connection elements. In this case, in step 210 of processing, the connection elements are shaped for example by means of laser structuring, spark erosion, forming and/or machining. Additionally or alternatively, in step 210 of processing, at least the connection elements are shaped by means of an additive manufacturing process, for example by means of 3D printing or three-dimensional printing.

In accordance with one exemplary embodiment, in step 210 of processing, the connection elements are shaped as at least one antenna for signals to and/or from the electrical circuit. In particular, in this case, the at least one antenna is shaped as a helical antenna, as a helical antenna having radial microcavities, as a rectangular antenna and/or as a butterfly antenna. Additionally or alternatively, in this case, a plurality of antennas aligned in different dimensions are shaped. In accordance with a further exemplary embodiment, in step 210 of processing, at least one depression section is shaped in the integration surface. In this case, the at least one depression section has in particular a parabolic depression profile.

In accordance with one exemplary embodiment, in step 220 of arranging, an electrical circuit is arranged which has at least one detection unit for detecting a physical variable and/or a signal transmission unit for transmitting signals to and/or from the electrical circuit. In particular, in step 220 of arranging, an electrical circuit embodied as an radio chip and/or sensor chip is arranged. Optionally, in step 220 of arranging, the electrical circuit is encapsulated with an encapsulation material and/or is provided with a thermal protection layer.

Figure 3:
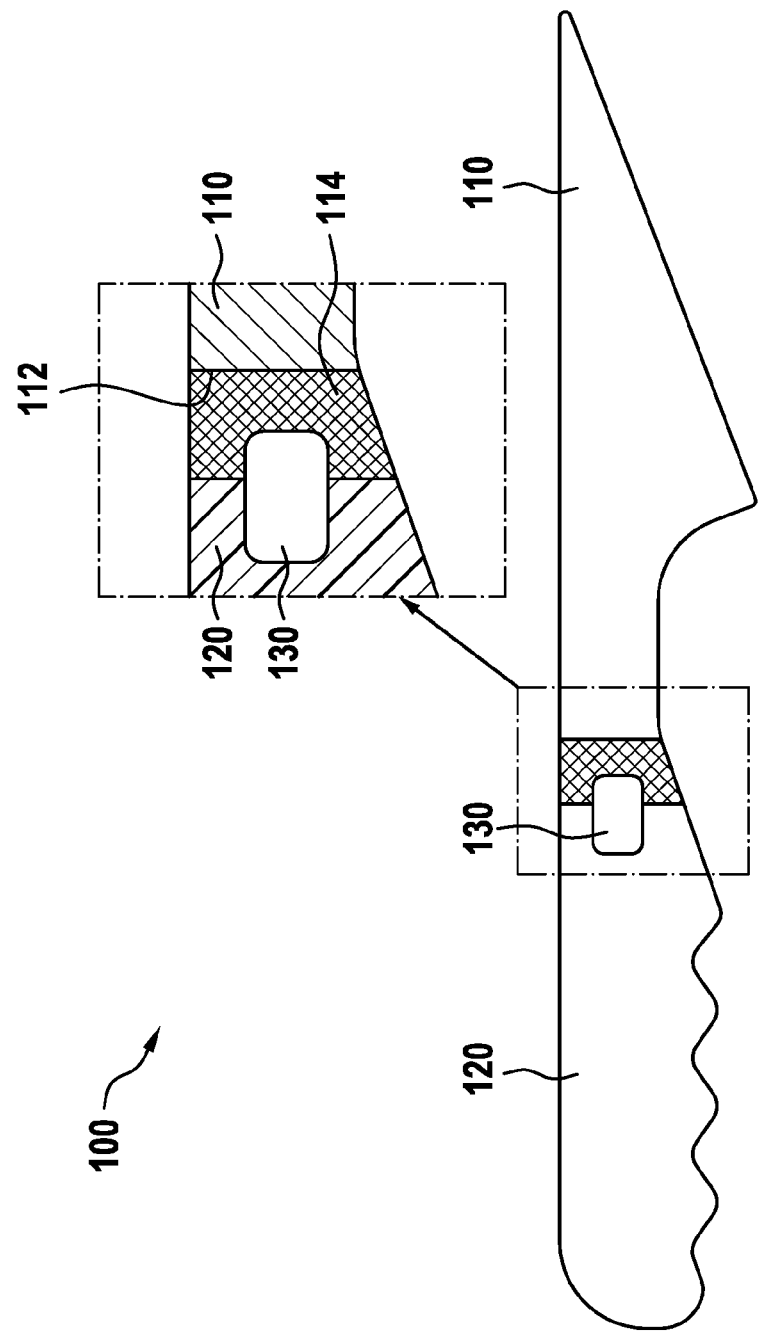
FIG. 3 shows a schematic illustration of a device in accordance with one exemplary embodiment.

FIG. 3 shows a schematic illustration of a device 100 in accordance with one exemplary embodiment. In this case, the device 100 in FIG. 3 corresponds or is similar to the device from FIG. 1. In accordance with the exemplary embodiment illustrated in FIG. 3, the device 100 is embodied as a set of surgical instruments, in particular a scalpel or the like. In this case, a partial section of the device 100 that has a blade represents the volume of the first material 110. The first material 110 is a metal material. Furthermore, a partial section of the device 100 that has a handle represents the volume of the second material 120. The second material 120 is a plastic material.

In the illustration in FIG. 3, a region of an interface between the first material 110 and the second material 120 is additionally shown as an enlarged excerpt. In the enlarged excerpt, the electrical circuit 130, for example embodied as a sensor chip, the integration surface 112 and the connection elements 114, for example embodied as grid element or grids composed of the first material 110, are illustrated and explicitly designated. The electrical circuit 130 is arranged at least partly in the region of the connection elements 114. Moreover, the electrical circuit 130 is embedded in the volume of the second material 120.

Figure 4:
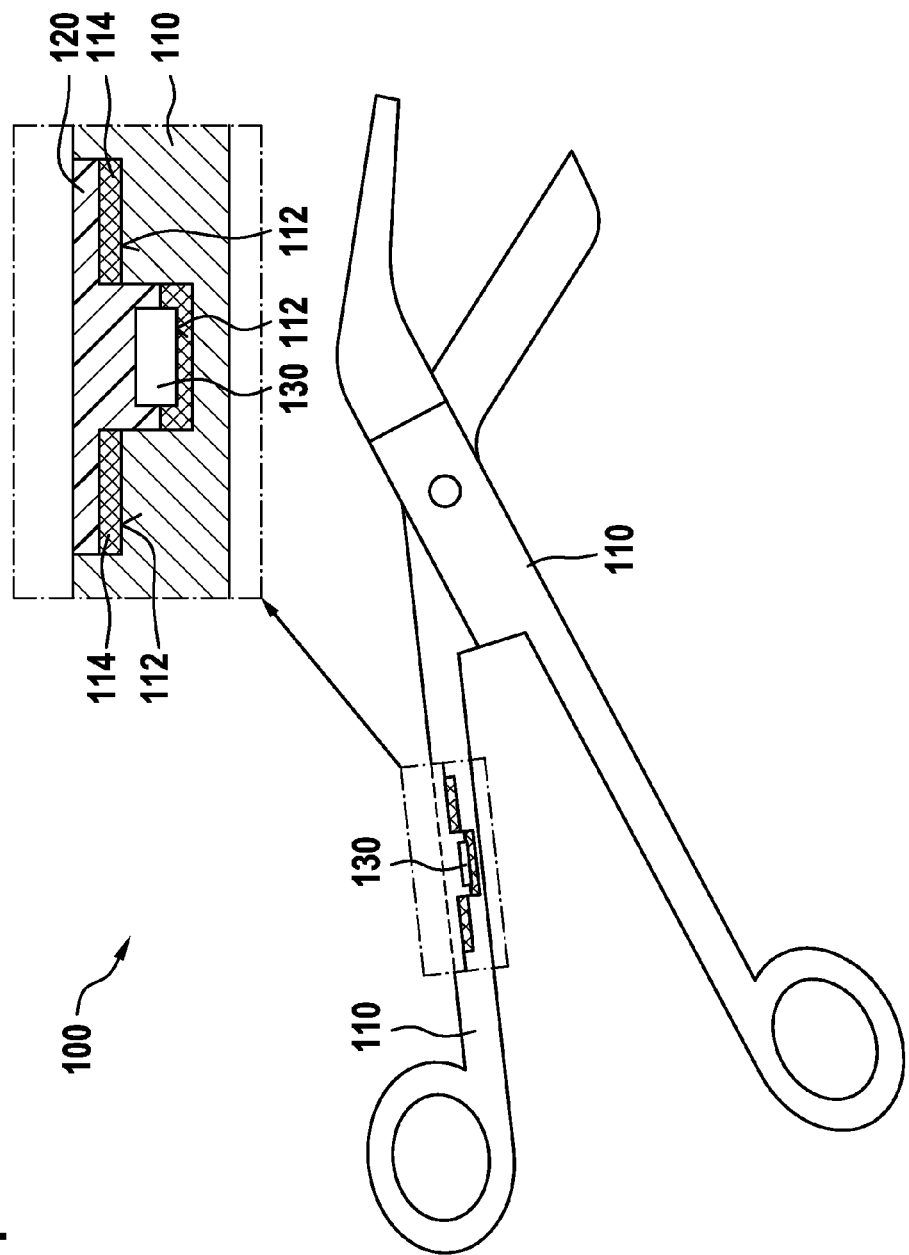
FIG. 4 shows a schematic illustration of a device in accordance with one exemplary embodiment.

FIG. 4 shows a schematic illustration of a device 100 in accordance with one exemplary embodiment. In this case, the device 100 in FIG. 4 corresponds or is similar to the device from FIG. 1. In accordance with the exemplary embodiment illustrated in FIG. 4, the device 100 is embodied as scissors in particular for use in the medical field. In this case, a body of the scissors represents the volume of the first material 110. The first material 110 is a metal material. The integration surface 112 represents a recessed partial section of the scissors. To put it more precisely, the integration surface 112 is stepped or shaped with a stepped profile. A cover layer applied on a region of the integration surface 112 represents the volume of the second material 120. The second material 120 is a plastic material.

In the illustration in FIG. 4, a region of the integration surface 112 or of an interface between the first material 110 and the second material 120 is additionally shown as an enlarged excerpt. In the enlarged excerpt, the electrical circuit 130, for example embodied as a sensor chip, the integration surface 112, for example shaped in a stepped manner or having a stepped profile, and the connection elements 114, for example embodied as grid elements or grids composed of the first material 110, are illustrated and explicitly designated. The electrical circuit 130 is arranged in the recessed partial section of the volume of the first material 110, said recessed partial section having the integration surface 112, and is enclosed by the volume of the second material 120.

With reference to the figures described above, and in particular to FIG. 3 and FIG. 4, hereinafter the design and production of a device 100 in the form of a metal-plastic composite tool having an integrated sensor as electrical circuit 130 are summarized and explained again in different words.

As connection elements 114, metallic grid structures are integrated in a design of the tool or of the device 100, which grid structures can be shaped or realized in terms of manufacturing technology by means of additive manufacturing methods, such as e.g. electron beam melting or selective laser melting. The electrical circuit 130 or the sensor (if necessary in encapsulated form) can be applied to these grid structures or connection elements 114. As a result of the grid structures or connection elements 114 subsequently being encapsulated by injection molding, the electrical circuit 130 is fixedly incorporated in the tool or the device 100. It is thus possible to achieve an integration of the electrical circuit 130 that affords protection against damage, is tight and thus enables good sterilization. In addition or as an alternative to the one RFID sensor already mentioned, e.g. temperature sensors can also be integrated as electrical circuit 130 in order to be able to monitor and document possible sterilization processes in the field of medical technology.

Integration of an electrical circuit, for example of a sensor, at various regions of a tool or a device 100 is thus made possible. Referring to FIG. 3 it should be noted that the electrical circuit 130 is integrated in a handle region of a device 100 embodied as a tool having a plastic handle, or in a transition region between metallic tool and plastic handle. Referring to FIG. 4 it should be noted that the electrical circuit 130 is integrated at an arbitrary location of the device 100 embodied as a metallic tool, wherein the connection elements 114 shaped as a grid structure are shaped at the location, wherein introducing the electrical circuit 130 is followed by filling or encapsulating by injection molding with plastic as second material 120. As an alternative to encapsulating the electrical circuit 130 with plastic by injection molding, it is also possible for the electrical circuit 130 to be embedded in epoxy resin in order to realize a sheathing with biocompatible material. As an alternative to realizing a connection of metal and plastic as first material 110 and second material 120, further manufacturing technologies are also conceivable, such as, for example, laser structuring of the integration surface 112, structuring of the integration surface 112 by means of spark erosion, structuring of the integration surface 112 by forming, and/or structuring of the integration surface 112 by machining.

FIGS. 5 to 15 described below illustrate, for the device 100 from any of the figures described above, various embodiments of connection elements 114 in accordance with exemplary embodiments, in other words in particular variants for a connection location between metal and plastic.

Figure 5:
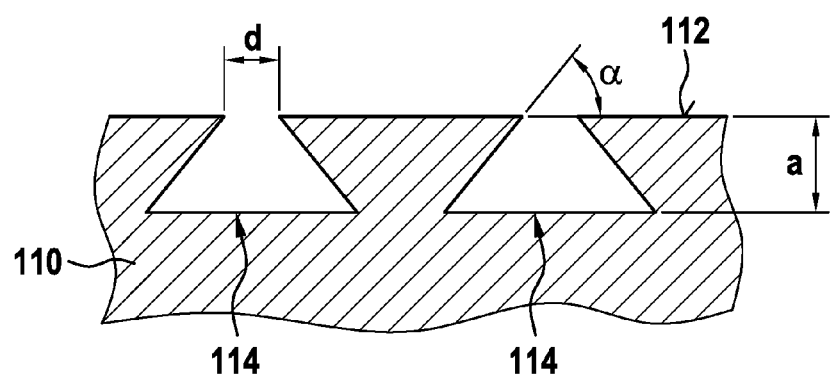
FIG. 5 shows a schematic illustration of connection elements in accordance with one exemplary embodiment.

FIG. 5 shows a schematic illustration of connection elements 114 in accordance with one exemplary embodiment. The connection elements 114 correspond or are similar to the connection elements from any of the figures described above, with the exception that the connection elements 114 in FIG. 5 are shaped as cavities having undercuts of dovetail shape. Part of the volume of the first material 110, the integration surface 112 and, by way of example, only two connection elements 114 are shown.

The connection elements 114 shaped as cavities having undercuts or here a profile of dovetail shape have an opening dimension d, a depth dimension a and an undercut angle $\alpha$. The opening dimension d represents a dimension of an opening of each connection element 114 in the integration surface 112. Purely exemplary values for the opening dimension d can be between 0.5 and 3 millimeters. The depth dimension a represents a depth of each connection element 114 relative to the integration surface 112. Purely exemplary values for the depth dimension a can be between 1 and 5 millimeters. The undercut angle $\alpha$ represents an angle of inclination of lateral sidewalls of each connection element 114 relative to a plane of the adjoining integration surface 112. Purely exemplary values for the undercut angle $\alpha$ can be between 45 and 70 degrees.

Figure 6:
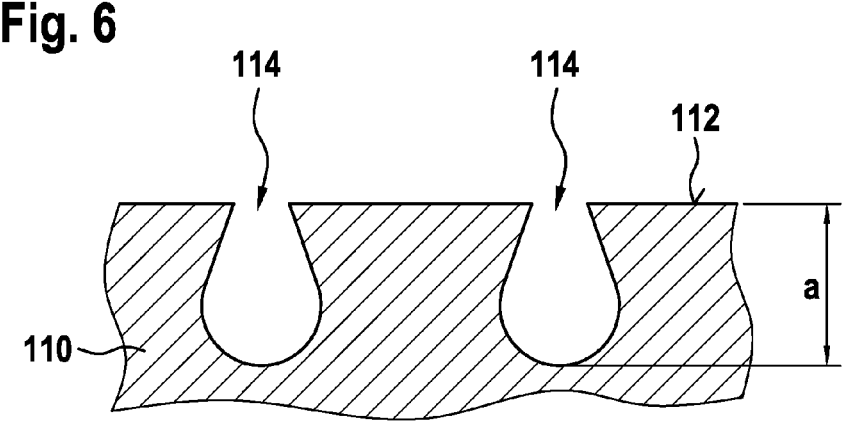
FIG. 6 shows a schematic illustration of connection elements in accordance with one exemplary embodiment.

FIG. 6 shows a schematic illustration of connection elements 114 in accordance with one exemplary embodiment. The connection elements 114 here correspond to the connection elements from FIG. 5, with the exception that the connection elements 114 in FIG. 6 are shaped as cavities having undercuts shaped as drops. A partial section of the volume of the first material 110, the integration surface 112 and, by way of example, only two connection elements 114 are likewise shown here.

The connection elements 114 shaped as cavities having undercuts or here a profile shaped as drops have a depth dimension a. The depth dimension a represents a depth of each connection element 114 relative to the integration surface 112. Purely exemplary values for the depth dimension a can be between 1 and 5 millimeters.

Figure 7:
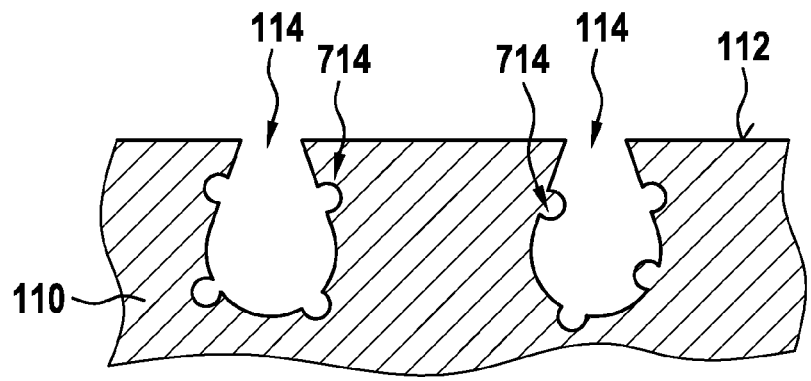
FIG. 7 shows a schematic illustration of connection elements in accordance with one exemplary embodiment.

FIG. 7 shows a schematic illustration of connection elements 114 in accordance with one exemplary embodiment. The connection elements 114 here correspond to the connection elements from FIG. 6, with the exception that the connection elements 114 in FIG. 7 additionally have microcavities 714 shaped in a surface of the connection elements 114 shaped as drops. A dimension of the microcavities 714 can be at least approximately 0.5 millimeter, for example.

Figure 8:
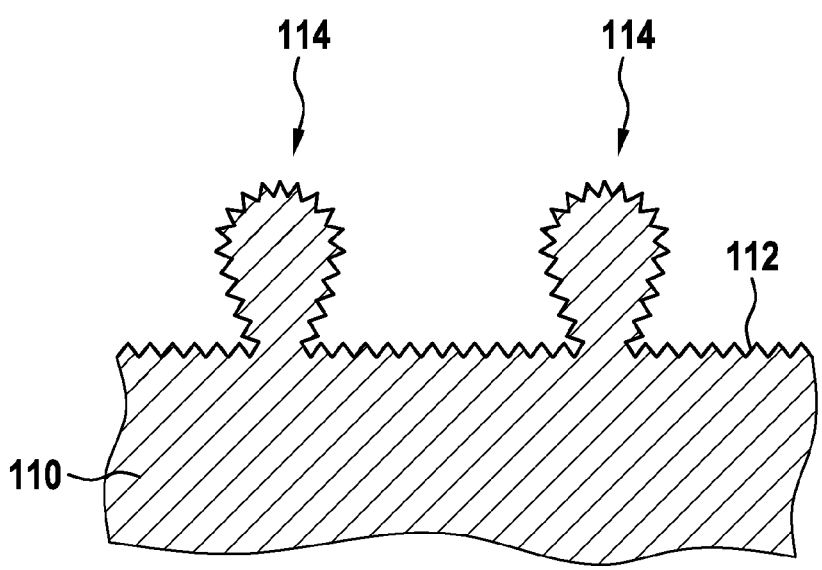
FIG. 8 shows a schematic illustration of connection elements in accordance with one exemplary embodiment.

FIG. 8 shows a schematic illustration of connection elements 114 in accordance with one exemplary embodiment. The connection elements 114 correspond or are similar to the connection elements from any of the figures described above, with the exception that the connection elements 114 in FIG. 8 are shaped as drop-shaped protuberances relative to the integration surface 112. Furthermore, a roughness of the integration surface 112 and of the connection elements 114 is increased. In this regard, it is possible to increase a surface area and thus an adhesion of the second material at the integration surface 112 composed of the first material 110. The roughness of the integration surface 112 and of the connection elements 114 can be characterized for example by an Rz value of at least 100 micrometers.

Figure 9:
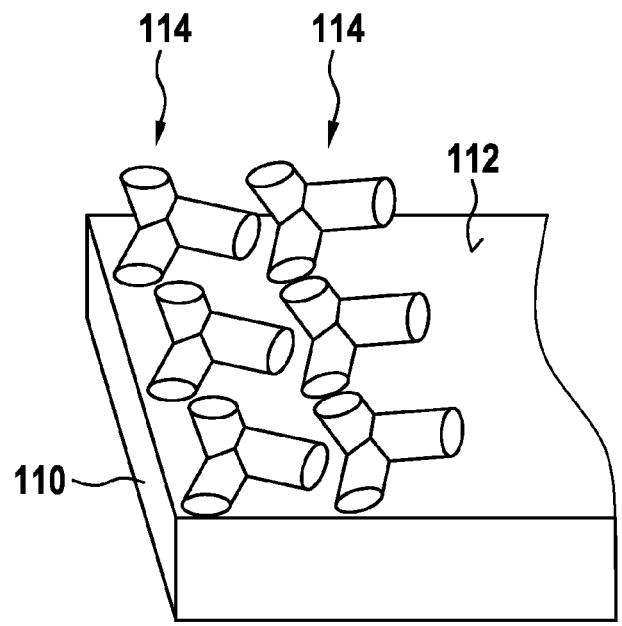
FIG. 9 shows a schematic illustration of connection elements in accordance with one exemplary embodiment.

FIG. 9 shows a schematic illustration of connection elements 114 in accordance with one exemplary embodiment.

The connection elements 114 correspond or are similar to the connection elements from any of the figures described above, with the exception that the connection elements 114 in FIG. 9 are shaped as grid structures, to put it more precisely as three-dimensional grid structures. A partial section of the volume of the first material 110, the integration surface 112 and a plurality of connection elements 114 are shown here. The electrical circuit of the device can be introduced in a region of the connection elements 114 and be encapsulated by injection molding for example with a plastic material as second material.

Figure 10:
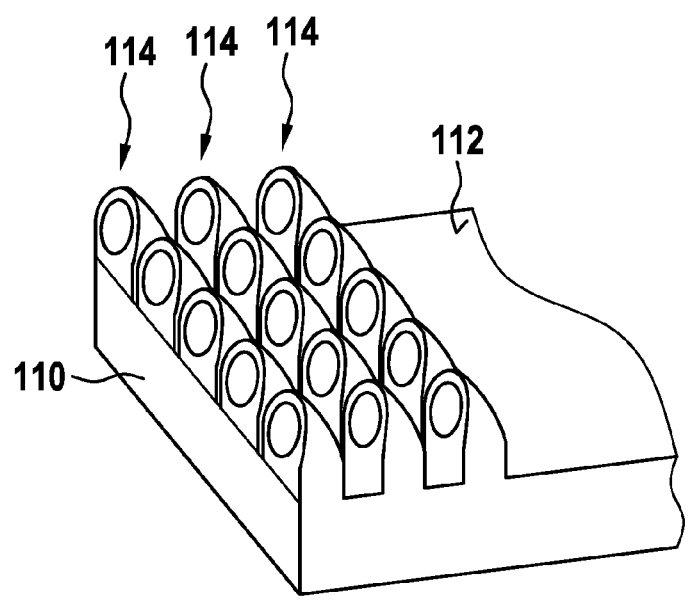
FIG. 10 shows a schematic illustration of connection elements in accordance with one exemplary embodiment.

FIG. 10 shows a schematic illustration of connection elements 114 in accordance with one exemplary embodiment.

The connection elements 114 correspond or are similar to the connection elements from any of the figures described above, with the exception that the connection elements 114 in FIG. 10 are shaped as loops or loopings or, to put it another way, in a looped fashion. A partial section of the volume of the first material 110, the integration surface 112 and a plurality of connection elements 114 are shown here.

Figure 11:
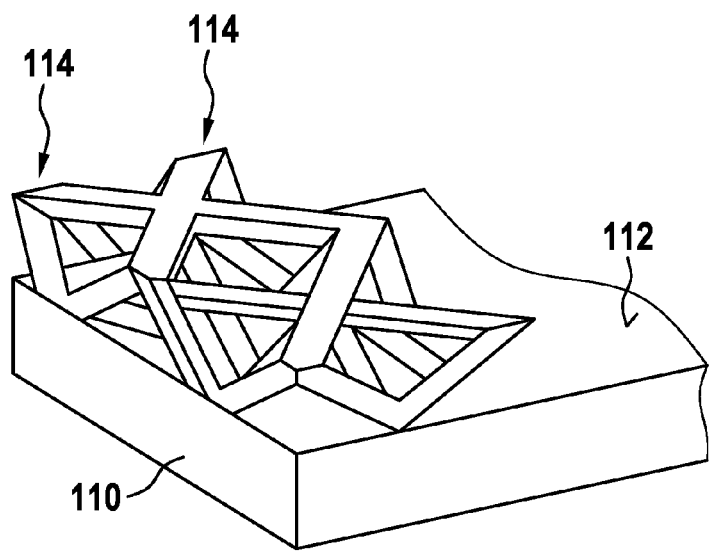
FIG. 11 shows a schematic illustration of connection elements in accordance with one exemplary embodiment.

FIG. 11 shows a schematic illustration of connection elements 114 in accordance with one exemplary embodiment. The connection elements 114 correspond to the connection elements from FIG. 9, with the exception that the connection elements in FIG. 11 are shaped as differently configured grid structures. To put it another way, the grid structures in FIG. 11 have a different shape than the grid structures from FIG. 9.

Figure 12:
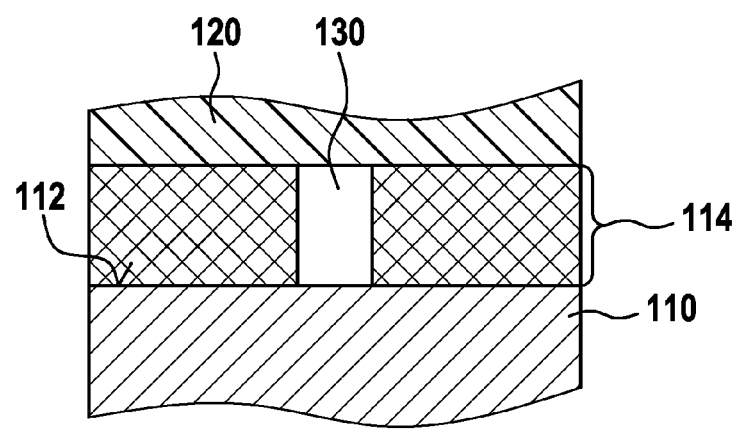
FIG. 12 shows a schematic illustration of connection elements in accordance with one exemplary embodiment.

FIG. 12 shows a schematic illustration of connection elements 114 in accordance with one exemplary embodiment. The connection elements 114 correspond or are similar to the connection elements from any of the figures described above, with the exception that the connection elements 114 in FIG. 12 are shaped as at least one antenna. In accordance with the exemplary embodiment illustrated in FIG. 12, the connection elements 114 are shaped as a rectangular antenna. FIG. 12 shows a partial section of the volume of the first material 110, the integration surface 112, the connection elements 114 and the electrical circuit 130, which is embodied for example as an RFID chip (RFID=Radio-Frequency Identification; identification with the aid of electromagnetic waves). Furthermore, the volume of the second material 120 is indicated. The connection elements 114 and the electrical circuit 130 are encapsulated by injection molding, surrounded or potted by the volume of the second material 120.

Figure 13:
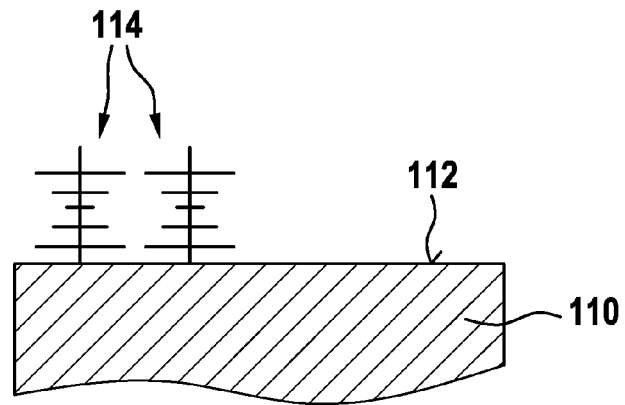
FIG. 13 shows a schematic illustration of connection elements in accordance with one exemplary embodiment.

FIG. 13 shows a schematic illustration of connection elements 114 in accordance with one exemplary embodiment. In this case, the connection elements 114 correspond to the connection elements from FIG. 12, with the exception that the connection elements 114 in FIG. 13 are shaped as at least one butterfly antenna, here for example two butterfly antennas. FIG. 13 shows a partial section of the volume of the first material 110, the integration surface 112 and, by way of example, only two connection elements 114 shaped as butterfly antennas.

Figure 14:
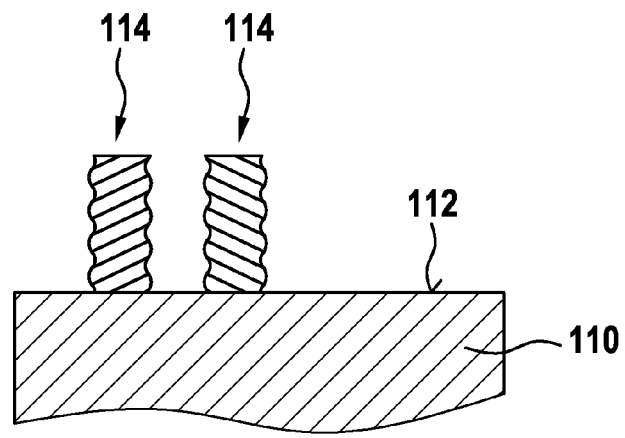
FIG. 14 shows a schematic illustration of connection elements in accordance with one exemplary embodiment.

FIG. 14 shows a schematic illustration of connection elements 114 in accordance with one exemplary embodiment. In this case, the connection elements 114 correspond to the connection elements from FIG. 12 or FIG. 13, with the exception that the connection elements 114 in FIG. 14 are shaped as at least one helical antenna, here for example two helical antennas. FIG. 14 shows a partial section of the volume of the first material 110, the integration surface 112 and, by way of example, only two connection elements 114 shaped as helical antennas.

Figure 15:
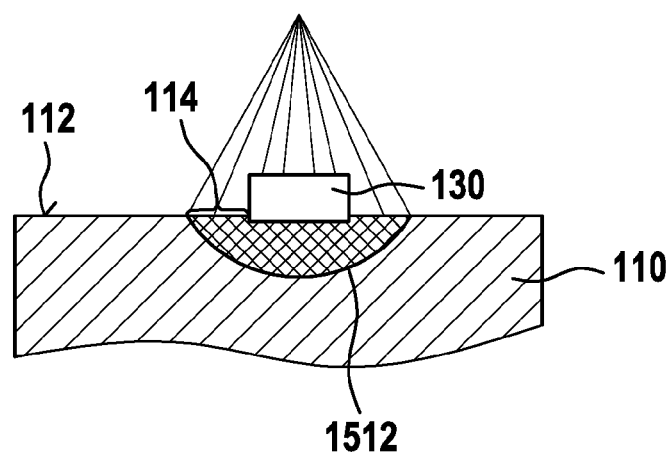
FIG. 15 shows a schematic illustration of connection elements in accordance with one exemplary embodiment.

FIG. 15 shows a schematic illustration of connection elements 114 in accordance with one exemplary embodiment. In this case, the connection elements 114 correspond to the connection elements from FIG. 12, with the exception that a depression section 1512 is shaped in the integration surface 112, in which depression section are arranged the connection elements 115 functioning as at least one antenna. The depression section 1512 is shaped as a trough, in particular as a trough having a parabolic depression profile. The depression section 1512 thus functions as a parabolic mirror for focused beam emission. Furthermore, FIG. 15 shows a partial section of the volume of the first material 110 and the electrical circuit 130 embodied as an RFID chip.

The additional functionality of the connection elements 114 as antenna or antennas in the metal-plastic connection zone is explained below with reference to the figures described above, and in particular to FIG. 12 to FIG. 15.

In this case, the connection elements 114 or 3D structures of the metal-plastic tool or of the device 100 which are provided in any case according to exemplary embodiments are utilized as an antenna for directing radiation or increasing a radiation range of e.g. RFID chips as electrical circuits 130. In this context, FIG. 12 to FIG. 15 show exemplary embodiments of antenna structures in the metal-plastic connection zone of the device 100 or in the case of sensor-integrated tools such as the device 100.

A shaping and alignment of the antennas can be tuned in detail to a transmission frequency of the electrical circuit 130 (usually in the MHz range in the case of RFID chips). In order to achieve both a stable connection between the materials 110 and 120 and advantageous transmission properties of the antennas, for example the helical antenna illustrated in FIG. 14 has radial microcavities, which are intended to result in a stable connection when the metal part is encapsulated with plastic by injection molding. An amplification effect or beam focusing, in terms of its direction, is dependent on an alignment of the antennas. It is therefore advantageous to arrange the antenna structures multidimensionally, which can be realized in a simple manner in terms of manufacturing technology, e.g. by means of 3D printing.

With reference to the figures described above, exemplary embodiments and also advantages of exemplary embodiments are once again explained in summary and/or presented briefly using different words.

Sensor-integrated tools such as the device 100 can be used for example in the field of medical technology. For this purpose, an electrical circuit 130 embodied as a sensor can be integrated in the device by means of the method 200 for integrating for example in a sterilization-stable manner, i.e. can be tightly packaged and secured such that the sterilization process does not impair a support and a function of the sensor. Furthermore, it is possible to achieve a secure support of the electrical circuit 130 on the device 100, e.g. for an unambiguous assignment, unequivocal monitoring of a sterilization process of the device 100 and the like, which is afforded only by the electrical circuit 130 being integrated in a manner not readily demountable. Overall it is possible to simplify for example sensor integration in metal components in view of high process temperatures in the production process of metallic components (e.g. casting), since a function of the electronics can be protected from temperatures of >100° C. Furthermore, signal transmission or communication and energy supply of electrical circuits 130 embedded in metal can be improved while avoiding or at least minimizing electromagnetic shielding effects.

In accordance with one exemplary embodiment, in particular, sensors can be integrated in metallic tools and, in this case, it is possible to enable communication, e.g. for "tracking" or localizing and tracking tools by means of RFID, tracking a sterilization process, etc., and also an energy supply of the sensors, e.g. by means of inductive charging. The sensor is introduced into the plastic region or the volume of the second material 120 of the tool or of the device 100 in order to enable wireless communication and energy supply of the sensor. If a sensor were embedded in the metal region or the volume of the first material 110 of the tool or of the device 100, read-out and inductive charging of the sensor would be hampered on account of shielding effects.

As a result of the connection elements 114, for example grid structures, being encapsulated by injection molding, the sensor is fixedly incorporated into the tool or the device 100. In this way, the sensor is integrated such that the tool or the device is still able to be cleaned well, without the sensor being damaged or its fit being adversely affected. That is advantageous in the field of medical technology, in particular, if sensor-integrated tools or devices 100 are intended to be sterilized. Furthermore, the plastic sheathing affords protection against mechanical damage of the sensor, e.g. against the tool or the device 100 being dropped. Embedding the sensor in the plastic region of the tool or of the device 100 makes it possible to realize a durable, permanent and sterilizable integration of the sensor which additionally protects the sensor against damage e.g. as a result of being dropped.

As a result of the sensor being embedded in the plastic region of the tool or of the device 100, communication of the sensor, e.g. read-out of an RFID chip, and wireless energy supply, e.g. inductive charging, are made possible since the metallic region or the volume of the first material 110 of the tool or of the device does not shield the sensor in this position. It is possible to enable an increase in the radiation range of the integrated sensors or electrical circuits 130 by means of the focusing of the, usually spherical, radiation by means of specially shaped 3D structures or antennas and/or an increase in a range in a plurality of spatial directions by means of multidimensional alignment of the structures or antennas. In order to protect the sensor or the electrical circuit 130 against process temperatures that occur during the sheathing, the electrical circuit 130 can be encapsulated, e.g. by means of a plastic or glass capsule with a thermal protection layer.

The device 100 and/or the method 200 can generally be used for sensor integration in tools. In particular, use in the field of medical technology is also advantageous. It is thus possible to satisfy the need to equip medical tools/OP tools with sensors in order to be able to track them e.g. by means of RFID or to be able to demonstrate or verify a sterilization process. Electrical circuits 130 integrated in a device 100 in accordance with the method 200 can moreover be integrated permanently and in a sterilization-stable manner. An application for determining the whereabouts of tools or devices 100 is also generally conceivable, for example in the field of logistics and tool management. This is made possible, inter alia, by the connection elements 114, which firstly keep the electrical circuit 130 far from the metal with little shielding and additionally make the metal-plastic connection robust and sturdy on account of their shape.

If an exemplary embodiment comprises an "and/or" linkage between a first feature and a second feature, then this should be interpreted such that the exemplary embodiment has both the first feature and the second feature in accordance with one embodiment, and has either only the first feature or only the second feature in accordance with a further embodiment.

The invention claimed is:

1. A method for integrating an electrical circuit in a device having an integration surface composed of a first material, comprising:
    processing the integration surface to shape connection elements using laser structuring, spark erosion, forming, machining, and/or an additive manufacturing process, the connection elements configured to increase an adhesion of the integration surface;
    arranging the electrical circuit adjacent to the processed integration surface; and
    applying a volume of a second material, which differs from the first material, at least over the processed integration surface such that the second material adheres to the connection elements of the integration surface and encloses the electrical circuit in a fluid-tight manner.

2. The method as claimed in claim 1, wherein the processing the integration surface comprises:
    shaping grid elements, recesses, loops, projection sections, angular elements, cavities having undercuts, and/or cavities as the connection elements so as to increase a roughness value of the integration surface.

3. The method as claimed in claim 1, wherein the processing the integration surface comprises:
    shaping at least one portion of the connection elements as at least one antenna for signals to and/or from the electrical circuit.

4. The method as claimed in claim 3, further comprising:
    shaping the antenna as a helical antenna, as a helical antenna having radial microcavities, as a rectangular antenna, and/or as a butterfly antenna.

5. The method as claimed in claim 3, wherein the processing the integration surface further comprises:
    shaping a plurality of antennas aligned in different dimensions.

6. The method as claimed in claim 3, wherein, the processing the integration surface further comprises:
    shaping at least one depression section in the integration surface, the at least one depression section having a parabolic depression profile.

7. The method as claimed in claim 1, wherein the electrical circuit has at least one detection unit configured to detect a physical variable and/or a signal transmission unit configured to transmit signals to and/or from the electrical circuit.

8. The method as claimed in claim 1, wherein the arranging the electrical circuit comprises:
    encapsulating the electrical circuit with an encapsulation material and/or layering the electrical circuit with a thermal protection layer.

9. A device comprising:
    an integration surface composed of a first material;
    a plurality of connection elements shaped in or on the integration surface by laser structuring, spark erosion, forming, machining, and/or an additive manufacturing process, the connection elements configured to increase an adhesion of the integration surface;
    an electrical circuit arranged adjacent to the processed integration surface; and
    a volume of a second material, which differs from the first material, applied at least over the processed integration surface such that the second material adheres to the connection elements of the integration surface and encloses the electrical circuit in a fluid-tight manner.

10. The device as claimed in claim 9, wherein:
    the device is a medical device, and
    the integration surface is located on a handle of the medical device.

* * * * *